United States Patent [19]

Sevrin et al.

[11] Patent Number: 4,977,159
[45] Date of Patent: Dec. 11, 1990

[54] 2-[(4-PIPERIDYL)METHYL]-1,2,3,4-TETRAHYDRO-9H-PYRIDO[3,4-B]INDOLE DERIVATIVES, AND THEIR APPLICATION IN TREATING DEPRESSIVE STATE, ANXIETY STATE OR HYPERTENSION

[75] Inventors: Mireille Sevrin, Paris; Pascal George; Jacques Menin, both of Vitry Sur Seine; Claude Morel, Magny Les Hameaux; Dennis Bigg, Castres, all of France

[73] Assignee: Synthelabo, Paris, France

[21] Appl. No.: 228,751

[22] Filed: Aug. 5, 1988

[30] Foreign Application Priority Data

Aug. 7, 1987 [FR] France ................. 87 11291

[51] Int. Cl.⁵ .................... C07D 471/02; A61K 31/44
[52] U.S. Cl. ........................................ 514/292; 546/87
[58] Field of Search ............................ 546/87; 514/292

[56] References Cited

U.S. PATENT DOCUMENTS 4,539,407 9/1985 Stack et al. ........................... 546/87

Primary Examiner—Alan L. Rotman
Attorney, Agent, or Firm—Fleit, Jacobson, Cohn, Price, Holman & Stern

[57] ABSTRACT

A compound which is a pyrido[3,4-b]derivative of formula (I)

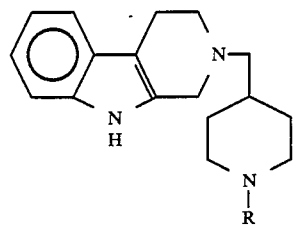

in which R is a hydrogen atom or an alkyl carbonyl, arylalkylcarbonyl or arylcarbonyl group of formula $COR_1$ wherein $R_1$ is a $C_1$-$C_6$ alkyl group, a benzyl group or a phenyl group unsubstituted or substituted with 1 to 3 substituents chosen from halogen atoms and trifluoromethyl, $C_1$-$C_3$ alkyl and $C_1$-$C_3$ alkoxy groups or R is an alkoxycarbonyl or benzyloxycarbonyl group of formula $COOR_2$ wherein $R_2$ is a $C_1$-$C_6$ alkyl group or a benzyl group, or R is a substituted aminocarbonyl group of formula $CONHR_3$ wherein $R_3$ is a $C_1$-$C_6$ alkyl group or a phenyl group, or R is an arylsulphonyl group of formula $SO_2R_4$ wherein $R_4$ is a phenyl group, or a pharmacologically acceptable acid addition salt thereof useful for treating hypertension, depressive state or anxiety state.

5 Claims, No Drawings

2-[(4-PIPERIDYL)METHYL]-1,2,3,4-TETRAHYDRO-9H-PYRIDO[3,4-B]INDOLE DERIVATIVES, AND THEIR APPLICATION IN TREATING DEPRESSIVE STATE, ANXIETY STATE OR HYPERTENSION

The present invention relates to 2-[(4-piperidyl)methyl]-1,2,3,4-tetrahydro-9H-pyridol[3,4-b]indole derivatives, to their preparation, to compositions containing them and to their use in therapy.

The present invention provides a pyrido[3,4-b]indole derivative of formula (I)

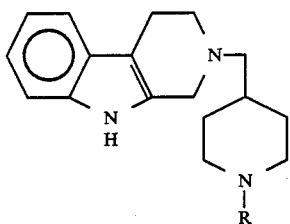

in which R is a hydrogen atom or an alkylcarbonyl, arylalkylcarbonyl or arylcarbonyl group of formula $COR_1$ wherein $R_1$ is a $C_1$-$C_6$ alkyl group, for example a methyl group, a benzyl group or a phenyl group unsubstituted or substituted by 1 to 3 substituents chosen from halogen atoms, for example chlorine and fluorine atoms, and trifluoromethyl, $C_1$-$C_3$ alkyl, for example methyl, and $C_1$-$C_3$ alkoxy, for example methoxy or ethoxy, groups, or R is an alkoxycarbonyl or benzyloxycarbonyl group of formula $COOR_2$ wherein $R_2$ is a $C_1$-$C_6$ alkyl group, for example a methyl, ethyl or i-propyl group, or a benzyl group, or R is a substituted aminocarbonyl group of formula $CONHR_3$ wherein $R_3$ is a $C_1$-$C_6$ alkyl group, for example a n-propyl group, or a phenyl group, or R is an arylsulphonyl group of formula $SO_2R_4$ wherein $R_4$ is a phenyl group, or a pharmacologically acceptable acid addition salt thereof.

The substituents on the phenyl groups are, for example, in the 2,3, or 4 positions or in the 3,5 position. The salts are, for example, benzenesulphonate, hydrochloride or dichlorohydrate salts.

The compounds of formula (I) may be prepared by a process as illustrated in the schemes on the following page.

The present invention provides a process for preparing a compound of formula (I) wherein R is a group of formula $COR_1$, which comprises reacting a compound of formula (VII) as shown in scheme 1 with an acid chloride of formula $ClCOR_1$, wherein $R_1$ is as defined above, in the presence of a base, for example triethylamine, and in a halogenated solvent, for example chloroform, at about room temperature, and if desired, forming a pharmacologically acceptable acid addition salt of the compound thus obtained.

The present invention also provides a process for preparing a compound of formula (I), or a pharmacologically acceptable acid addition salt thereof, wherein R is a group of formula $COOR_2$, which comprises reacting a compound of formula (VII) with a haloformate of formula $XCOOR_2$, wherein X is a halogen, for example chlorine, and $R_2$ is as defined above, in the presence of a base, for example triethylamine, and in a halogenated solvent, for example chloroform, at about room temperature, and if desired, forming a pharmacologically acceptable acid addition salt of the compound thus obtained.

Scheme 1

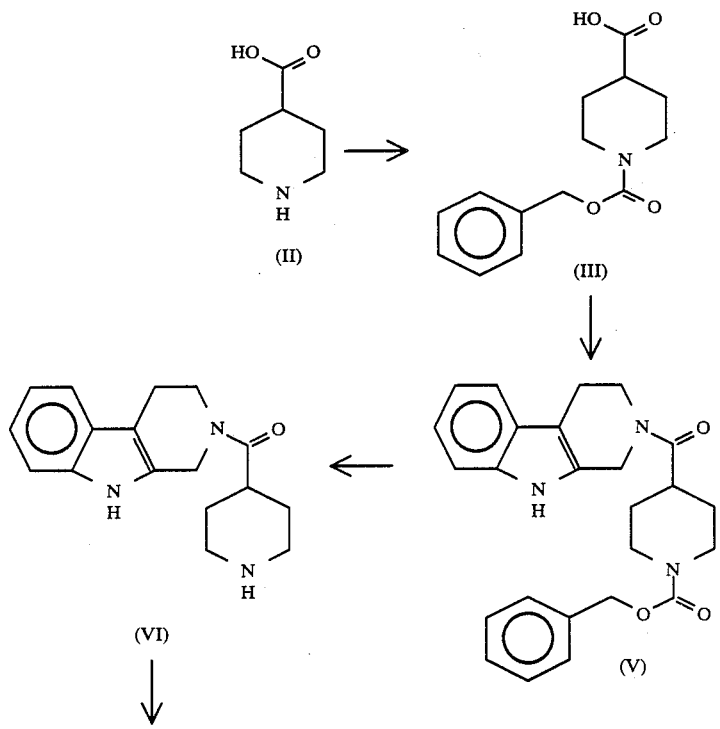

Scheme 1

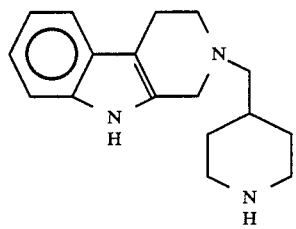

(VII)

Scheme 2

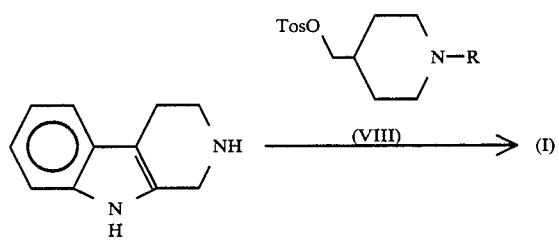

Scheme 3

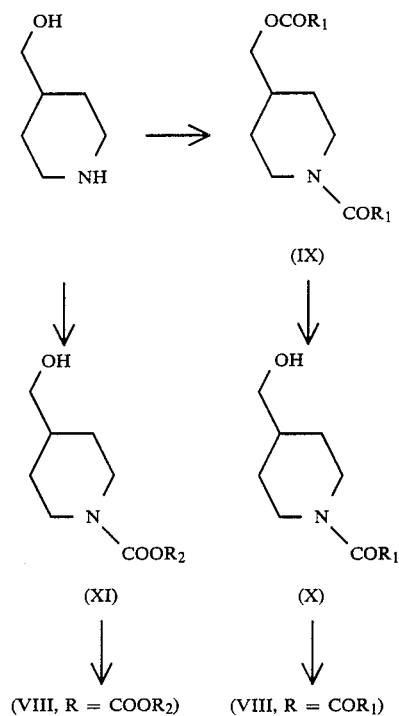

The present invention additionally provides a process for preparing a compound of formula (I), or a pharmacologically acceptable acid addition salt thereof, wherein R is a group of formula $CONHR_3$, which comprises reacting a compound of formula (VII) with an isocyanate of formula $R_3NCO$, wherein $R_3$ is as defined above, in a halogenated solvent, for example chloroform, and if desired, forming a pharmacologically acceptable acid addition salt of the compound thus obtained.

The present invention further provides a process for preparing a compound of formula (I), or a pharmacologically acceptable acid addition salt thereof, wherein R is a group of formula $SO_2R_4$, which comprises reacting a compound of formula (VII) with a phenylsulphonyl chloride of general formula $ClSO_2R_4$, wherein $R_4$ is as defined above, in the presence of a base, for example triethylamine, and in a halogenated solvent, for example chloroform or dichloromethane, at about room temperature.

The present invention also provides a process for preparing a compound of formula (I), or a pharmacologically acceptable acid addition salt thereof, wherein R is hydrogen, i.e., a compound of formula (VII), or a pharmacologically acceptable acid addition salt thereof, which comprises reducing 2-[(4-piperidyl)carbonyl]-1,2,3,4-tetrahydro-9H-pyrido-[3,4-b]indole of formula (VI) as shown in scheme 1 with lithium aluminium hydride in an ethereal solvent, for example diethyl ether or tetrahydrofuran, at a temperature of from 20° to 67° C., and if desired, forming a pharmacologically acceptable acid addition salt thereof.

The compound of formula (VII) prepared in this manner may serve as the starting compound for preparing the other compounds of formula (I) in which R is other than a hydrogen atom.

Scheme 1 illustrates an example of a route for the preparations of compounds of formula (VI) and (VII). 4-Piperidinecarboxylic acid of formula (II) is first reacted with benzyl chloroformate, in the presence of a base and in an aqueous medium, to obtain 1-(benzyloxycarbonyl)-4-piperidinecarboxylic acid of formula (III). 1,2,3,4-tetrahydro-9-H-pyrido[3,4-b]indole is reacted with the acid chloride of the compound of formula (III), prepared in situ with a chlorinating agent, for example thionyl chloride, in an inert solvent, for example tetrahydrofuran, and in the presence of a base, for example triethylamine, at about room temperature, to obtain benzyl 4-[(1,2,3,4-tetrahydro-9H-pyrido[3,4-b]indol-2-yl)-carbonyl]-1-piperidinecarboxylate of formula (V). The compound of formula (V) is subjected to a catalytic reduction to obtain the compound of formula (VI).

When R is a group of formula COR$_1$ or COOR$_2$, it is possible to use a process as illustrated in Scheme 2. Thus the present invention additionally provides a process for preparing a compound of formula (I), or a pharmacologically acceptable acid addition salt thereof wherein R is a group of formula COR$_1$ or COOR$_2$, which comprises reacting 1,2,3,4-tetrahydro-9H-pyrido[3,4-b]indole with a tosylate of formula (VIII) in which Tos is a tosyl group and R is as defined above, either in the absence or presence of an inert solvent, such as dimethylformamide or xylene, at a temperature of from 20° to 150° C., and optionally in the presence of an organic base such as a tertiary amine or an inorganic base such as an alkali metal carbonate or hydrogen carbonate, and if desired, forming a pharmacologically acceptable acid addition salt of the compound thus obtained.

The tosylate of formula (VIII) may be prepared, for example, according to the method illustrated in Scheme 3. When R is a group of general formula COR$_1$, 4-piperidinemethanol is reacted with an acid chloride of formula ClCOR$_1$, in an inert solvent such as a chlorinated solvent, at a temperature of from 20° to 80° C. An ester amide of formula (IX) is thereby obtained, which is saponified, for example with sodium hydroxide or potassium hydroxide, in a lower aliphatic alcohol solvent, preferably ethanol, to obtain an alcohol of formula (X), the tosylate of which is finally prepared by reacting it with tosyl chloride, in a basic medium such as pyridine.

When R is a group of formula COOR$_2$, 4-piperidinemethanol is reacted with a chloroformate of formula ClCOOR$_2$, in a solvent such as a chlorinated solvent, at about room temperature. A carbamate of formula (XI) is thereby obtained, the tosylate of which is prepared as described above.

4-Piperidine methanol may be obtained, for example, by the reduction of ethyl 4-piperidine carboxylate with lithium aluminium hydride, or by the reduction of ethyl 1-benzyl-4-piperidinecarboxylate in the same manner, followed by catalytic hydrogenolysis under pressure.

The Examples which follow further illustrate the present invention. The elemental microanalyses and the IR and NMR spectra confirm structures of the products obtained.

The numbers shown in brackets in the titles of the Examples correspond to those in the table given later.

EXAMPLE 1

(Compound No. 1)

2-[(4-Piperidyl)methyl]-1,2,3,4-tetrahydro-9H-pyrido[3,4-b]indole dihydrochloride.

1.1. 1-(Benzyloxycarbonyl)-4-piperidinecarboxylic acid 51.6 g (0.4 mol) of 4-piperidinecarboxylic acid, 600 ml of water and 35.2 g (0.88 mol) of sodium hydroxide flakes are introduced under an argon atmosphere into a round-bottomed flask.

The solution is cooled to 5° C., 68.6 ml (0.48 mol) of benzyl chloroformate are added rapidly, and the mixture is stirred for 1 h at 0° C. and then for 2 h at 20° C., and treated with 250 ml of water. The aqueous phase is washed twice with 200 ml of toluene, acetic acid is added out the mixture is extracted with dichloromethane. The organic phase is separated off, washed with water and dried over sodium sulphate, and the solvent is evaporated off under reduced pressure. The residual oil crystallizes in hexane. 100 g of dry product are obtained.

Melting point: 78°–80° C.

1.2. Benzyl 4-[(1,2,3,4-tetrahydro-9H-pyridi[3,4-b]indol-2-yl)carbonyl]-1-piperidinecarboxylate 25 ml (343 mol) of thionyl chloride are added under an argon atmosphere to a solution of 25 g (95 mol) of 1-(benzyloxycarbonyl)-4-piperidinecarboxylic acid in 500 ml of toluene. The mixture is heated under reflux for 5 h and the solvent then evaporated off under reduced pressure. The residue is taken up with 500 ml of toluene and evaporated again. 25.5 g of oily product are obtained, and this is dissolved in 250 ml of tetrahydrofuran, this solution is added under an argon atmosphere to a solution of 16.6 g (90 mmol) of 1,2,3,4-tetrahydro-9H-pyrido[3,4-b]indole in 800 ml of tetrahydrofuran and 12.7 ml (90 mmol) of triethylamine, and the mixture is stirred at 20° C. for 48 h. A precipitate is separated off by filtration and washed with tetrahydrofuran, the filtrate is evaporated under reduced pressure, the residue is dissolved in 1,200 ml of dichloromethane, the solution is washed with 1 N aqueous hydroxide solution and then with water and dried over sodium sulphate, and the solvent is evaporated off under reduced pressure. 32 g of a white solid are obtained.

Melting point: 160°–162° C.

1.3. 2-[(4-Piperidyl)carbonyl]-1,2,3,4-tetrahydro-9H-pyrido[3,4-b]indole 32 g (76.65 mmol) of benzyl 4-[(1,2,3,4-tetrahydro-9H-pyrido[3,4-b]indol-2-yl)carbonyl]-1-piperidinecarboxylate, 300 ml of methanol, 300 ml of dichloromethane and 9 g of palladinized charcoal (10% palladium)

are introduced into a Parr apparatus, and a hydrogenolysis is performed under approximately 0.41 MPa for 18 h.

The reaction mixture is filtered, the filtrate evaporated and the residue taken up with 1,000 ml of water. Sodium hydroxide is added until the pH is basic, and the aqueous phase is extracted with dichloromethane. The organic phase is separated off, washed with water and dried over sodium sulphate, the solvent is evaporated off under reduced pressure and the residue is recrystallized in ethyl acetate. 17.7 g of a white solid are obtained.

Melting point: 190°–192° C.

1.4.
2-[(4-Piperidyl)methyl]-1,2,3,4-tetrahydro-9H-pyrido]3,4-b]indole dihydrochloride 6 g (21.17 mmol) of 2-[(4-piperidyl)carbonyl]-1,2,3,4-tetrahydro-9H-pyrido[3,4-b]indole dissolved in 800 ml of tetrahydrofuran are added under an argon atmosphere to a suspension of 6 g(158 mmol) of lithium aluminium hydride in 150 ml of tetrahydrofuran, and the mixture is heated under reflux for 12 h. It is hydrolysed at 0° C. with 6.5 ml of water, 5 ml of 20% strength aqueous sodium hydroxide solution and 22 ml of water. The mixture is filtered, the solvent is evaporated off under reduced pressure, and the residue is suspended in 500 ml of water, filtered off, dried and recrystallized in the minimum amount of methanol. 2.37 g of free base are thereby obtained. Melting point: 189°–190° C.

The dihydrochloride of the base is prepared in 0.1 N hydrochloric acid in isopropyl alcohol.

Melting point: 290°–292° C.

EXAMPLE 2

(Compound No. 2)

2-[(1-Benzoyl-4-piperidyl)methyl]-1,2,3,4-tetrahydro-9H-pyrido[3,4-b]indole 2.7 g (10 mmol) of 2-[(piperidyl)methyl]-1,2,3,4-tetrahydro-9H-pyrido[3,4-b]indole, 30 ml of chloroform and 1.6. ml (11 mmol) of triethylamine are introduced under an argon atmosphere into a Keller flask. 1.546 g (11 mmol) of benzoyl chloride dissolved in 100 ml of chloroform are added, and the mixture is stirred at 20° C. for 48 H. The solvent is evaporated off under reduced pressure, and the residue is taken up with water, filtered off, dissolved in ethyl acetate and treated with activated charcoal. After filtration, the solvent is evaporated off under reduced pressure and the residue crystallized in isopropyl ether and recrystallized in acetonitrile. 1.8 g of white solid are obtained. Melting point: 161.5°–163.5° C.

EXAMPLE 3

(Compound No. 4)

Ethyl 4-[(1,2,3,4-tetrahydro-9H-pyrido[3,4-b]indol-2-yl)methyl]-1-piperidinecarboxylate 7.06 g (26.2 mmol) of 2-[(4-piperidyl)methyl]-1,2,3,4-tetrahydro-9H-pyrido[3,4-b]indole, 70 ml of chloroform and 4 ml (26.2 mmol) of triethylamine are introduced under an argon atmosphere into a Keller flask, and 2.8 ml (26.2 mmol) of ethyl chloroformate are added.

The mixture is stirred for 14 h at 20° C., the solvent evaporated off under reduced pressure, the residue taken up with water and the aqueous phase extracted with ethyl acetate. The organic phase is separated off and dried over sodium sulphate, the solvent evaporated off under reduced pressure and the residue recrystallized in acetonitrile. 2 g of a while solid are obtained.

Melting point: 117.5°–120° C.

EXAMPLE 4

(Compound No. 5)

N-Phenyl-4-[(1,2,3,4-tetrahydro-9H-pyrido[3,4-b]indol-2-yl)methyl]-1-piperidinecarboxamide 7.5 g (27.7 mmol) of 2-[(4-piperdyl)methyl]-1,2,3,4-tetrahydro-9H-pyrido[3,4-b]indole and 75 ml of chloroform are introduced under an argon atmosphere into a round-bottomed flask, 7.5 ml (67.6 mmol) of phenyl isocyanates are added and the mixture is stirred for 14 h at 20° C. The precipitate which has formed is filtered off, rinsed with isopropyl ether and recrystallized in methanol. 7.5 g of product are obtained.

Melting point: 207°–209° C.

EXAMPLE 5

(Compound No. 7)

2-](1-Phenylsulphonyl-4-piperidyl)methyl]-1,2,3,4-tetrahydro-9H-pyrido[3,4-b]indole 1.4 ml (11 mmol) of phenylsulphonyl chloride are added to a suspension of 2.7 g (10 mmol) of 2-[(4-piperidyl)methyl]-1,2,3,4-tetrahydro-9H-pyrido[3,4-b]indole and 1.6 ml (10 mmol) of triethylamine in 30 ml of chloroform. A solution is obtained, which is stirred at 20° C. for 24 h.

The solvent is evaporated off under reduced pressure, the residue taken up with water, the aqueous phase extracted with dichloromethane, the organic phase dried over sodium sulphate, the solvent evaporated off under reduced pressure and the residue recrystallized in ethyl acetate. 0.86 g of a white solid is obtained.

Melting point: 142°–145° C.

EXAMPLE 6

(Compound No. 9)

2-{[1-(3-Methylbenzoyl)-4-piperidyl]methyl}-1,2,3,4-tetrahydro-9H-pyrido[3,4-b]indole 6.1 4-Piperidinemethanol 28.5 g (0.75 mol) of lithium aluminium hydride and 1.2 l of tetrahydrofuran are introduced into a 4-l three-necked round-bottomed flask equipped with a mechanical stirring system and a condenser. 117.9 g 0.75 mol) of ethyl 4-piperidinecarboxylate dissolved in 1.2 l of tetrahydrofuran are added to the suspension obtained, and the mixture is stirred for 6 h at 20° C. It is cooled to 0° C., and then hydrolysed by adding successively 22 ml of water, 22 ml of 1 N sodium hydroxide and 46 ml of water. The mixture is stirred for 30 min. at 20° C. and filtered, and the precipitate is washed with tetrahydrofuran and then with ether. The solvents are evaporated off under reduced pressure and 84.4 g of an oil are obtained, this being used without further treatment in the following stage.

6.2.[1-(3-Methylbenzoyl)-4-piperidyl]methyl 3-methylbenzoate 42.25 g (0.367 mol) of 4-piperidinemethanol and 430 ml of 1,2-dichloroethane are introduced under an argon atmosphere into a 3-l three-necked round-bottomed flask, and 82 g (0.81 mol) of triethylamine are added, followed by 125.2 g (0.81 mol) of 3-methylbenzoyl chloride. The mixture is heated under reflux for 4 h 30 min., a further 8.2 g (0.08 mol) of triethylamine and 12.5 g (0.08 mol) of 3-methylbenzoyl chloride are added, and the mixture is heated for a further 3 h.

It is filtered, the salts are washed with 1,2-dichloroethane, the filtrate is evaporated under reduced pressure, the residue is dissolved in ethyl acetate, the solution is washed with saturated aqueous sodium chloride solution, the solvent is evaporated off under reduced pressure and the residue is recrystallized in a 1:1 isopropyl alcohol/ethyl acetate mixture. 80 g of white solid are obtained.

Melting point: 80°–83° C.

6.3. 1-(3-Methylbenzoyl)-4piperidinemethanol

A solution of 12.76 g (0.23 mol) of potassium hydroxide in 75 ml of ethanol and 75 ml of water is added to a solution of 80 g (0.23 mol) of [1-(3-methylbenzoyl)-4-piperidyl]methyl 3-methylbenzoate in 400 ml of ethanol. The mixture is stirred at 20° C. for 3 h, the solvent evaporated off under reduced pressure and the aqueous phase extracted with ethyl acetate. The organic phase is washed with water and then with saturated aqueous sodium hydroxide solution, and dried over magnesium sulphate. The solvent is evaporated off under reduced pressure and 53 g of alcohol are obtained, this being used without further treatment in the following stage.

6.4. [1-(3-Methylbenzoyl)-4-piperidyl]methyl 4-methylbenzenesulphonate 53.3 g (0.28 mol) of 4-methylbenzenesulphonyl chloride in 60 ml of pyridine are added to a solution of 52 g (0.22 mol) of 1-(3-methylbenzoyl)-4-piperidinemethanol in 100 ml of pyridine. The mixture is stirred at 20° C. for 4 h, and then poured into ice. The aqueous phase is extracted with dichloromethane, and the organic phase washed with 10 N aqueous hydrochloric acid solution and dried over magnesium sulphate. The solvents are evaporated off under reduced pressure and 70 g of white solid are obtained.

Melting point: 68°–70° C.

6.5. 2-{[(3-Methylbenzoyl)-4-piperidyl]methyl}-1,2,3,4-tetrahydro-9H-pyrido[3,4-b]indole 1.7 g (10 mmol) of 1,2,3,4-tetrahydro-9H-pyrido[3,4-b]indole, 3,9 g (10 mmol) of [1-(3-methylbenzoyl)-4-piperidyl]methyl 4-methylbenzenesulphonate, 2.9 g (20 mmol) of potassium carbonate and 25 ml of dimethylformamide are introduced under an argon atmosphere into a 100-ml round-bottomed flask. The mixture is stirred at 100° C. for 5 h and hydrolysed, and the aqueous phase extracted with ethyl acetate. The organic phase is washed with water and then with saturated aqueous sodium chloride solution and dried over sodium sulphate, and the solvents are evaporated off under reduced pressure. The residue is purified by chromatography on a silica column, eluting with a 9:1 dichloromethane/methanol mixture, and, after recrystallization in ethyl acetate, 1.2 g of pure base are obtained.

Melting point: 185°–187° C.

The following table illustrates the structures and melting points of a few compounds according to the invention.

TABLE

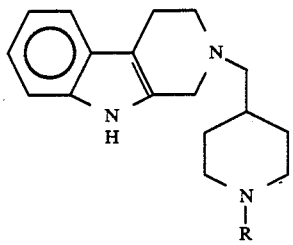
(I)

| No. | R | Salt or base | F(°C.) |
|---|---|---|---|
| 1 | H | dichlorohydrate | 290–292 |
| 2 | $COC_6H_5$ | base | 161,5–163,5 |
| 3 | $COCH_2C_6H_5$ | benzenesulphonate | 197–199 |
| 4 | $COOC_2H_5$ | base | 117,5–120 |
| 5 | $CONHnC_3H_7$ | base | 207–209,5 |
| 6 | $CONHC_6H_5$ | base | 207–209 |
| 7 | $SO_2C_6H_5$ | base | 142–145 |
| 8 | $COC_6H_4$-3-Cl | base | 199–201 |
| 9 | $COC_6H_4$-3-$CH_3$ | base | 184–187 |
| 10 | $COC_6H_4$-3-$OC_2H_5$ | base | 206–208 |
| 11 | $COC_6H_4$-3-F | hydrochloride | 228–230 |
| 12 | $COC_6H_4$-2-$CH_3$ | hydrochloride | 231–233 |
| 13 | $COC_6H_4$-4-$CH_3$ | base | 204–206 |
| 14 | $COC_6H_3$-3,5-$(CF_3)_2$ | hydrochloride | 266–268 |
| 15 | $COC_6H_3$-3,5-$(CH_3O)_2$ | hydrochloride | 165–170 |
| 16 | $CONHnC_4H_9$ | base | 215–218 |
| 17 | $COCH_3$ | base | 137–139 |
| 18 | $COOiC_3H_7$ | benzenesulphonate | 215–217 |
| 19 | $COnC_3H_7$ | base | 164–166 |
| 20 | $COOCH_3$ | benzenesulphonate | 210–212 |
| 21 | $COOCH_2C_6H_5$ | benzenesulphonate | 209–211 |

The compounds of the invention were subjected to a series of pharmacological tests which demonstrated their value as substances having therapeutic activity.

Thus, they were subjected to a study in respect of their affinity for 5-$HT_{1A}$ type serotoninergic receptors. In the rate hippocampus, the compounds displace a labelled specific ligand, [$^3$H]-8-hydroxy-2-dipropylaminotetralin, (hereinafter designated "[$^3$H]-8-OH-DPAT"), described by Gozlan et al, Nature, (1983), 305, 140–142.

The animals used are Sprague-Dawley male rats weighing 160 to 200 g. After decapitation, their brain is removed and the hippocampus excised. The tissue is ground in an Ultra-Turrax Polytron apparatus for 30 s at half the maximum speed in 10 volumes of 50 mM Tris buffer whole pH is adjusted to 7.4 with hydrochloric acid (equivalent to 100 mg of fresh tissue per ml). The homogenized tissues are washed three times at 4° C. by centrifuging them on each occasion at 48,000×g and resuspending the pellet for 10 min. in cooled fresh buffer. Finally, the last pellet is suspended in the buffer to produce a concentration of 100 mg of original tissue per ml of 50 mM buffer. The suspension is then left to incubate at 37° C. for 10 min.

The binding with [$^3$H]-8-OH-DPAT is determined by incubating 10 μl of membrane suspension in a final volume of 1 ml of buffer containing 10 μM pargyline.

After the incubation, the membranes are recovered by filtration on Whatman GF/B filters, which are washed three times with 5ml aliquot portions of ice-cold buffer. The filters are extracted in scintillation fluid and their radioactivity is measured by liquid scintigraphy. The specific binding of [$^3$H]-8-OH-DPAT is defined as the quantity of radioactivity retained on the filters and capable of being inhibited by coincubation in 10 μM 5-hydroxytryptamine. At a [$^3$H]-8-OH-DPAT concentration of 1 nM, the specific binding represents from 70 to 80% of the total radioactivity recovered on the filter.

For each concentration of test compound, the percentage inhibition of the binding with [³H]-8-OH-DPAT, and then the IC$_{50}$ concentration, the concentration which inhibits 50% of the binding, are determined.

For the compounds of the invention, the IC$_{50}$ values lie between 0.001 and 0.2 μM.

The central activity of the compounds of the invention was assessed by their effects on the "PGO (pontogeniculooccipital) spikes" induced by reserpine (PGO-R test) in cats, according to the method described by H. Depoortere, Sleep 1976, 3rd Europ. Congr. Sleep Res., Montpellier 1976, 358-361 (Karger, Basel 1977).

Cumulative doses of test compounds are administered (from 0.1 to 3 mg/kg intravenously) at 30-min. time intervals, 4 h after the intraperitoneal injection of a dose of 0.75 mg/kg of reserpine, to curarized cats under artificial ventilation. The electroencepthalographic and phasic (PGO-R spike) activities are obtained using cortical and deep (lateral geniculate) electrodes. For each dose of test compound, the percentage decrease in the number of PGO spikes, and then the AD$_{50}$, the active dose which decreases this number of spikes by 50%, are determined.

For the compounds of the invention, the intravenous ED$_{50}$ values lie between 0.01 and 1 mg/kg.

The results of the tests show that the compounds of formula (I) possess, in vitro, a high affinity and a selectivity for 5-HT$_{1A}$ type serotoninergic receptors. In vivo, they show an agonist, partial agonist or antagonist activity with respect to those receptors.

The compounds of the invention may hence be used for the treatment of diseases and conditions directly or indirectly involving the 5-HT$_{1A}$ type serotoninergic receptors, in particular for the treatment of depressive states, anxiety states and sleep disorders, for the regulation of food intake and for the treatment of vascular, cardiovascular or cerebrovascular conditions such as hypertension or migraine.

Thus the present invention provides a compound of formula (I), or a pharmacologically acceptable acid addition salt thereof, for use in a method of treatment of the human or animal body by therapy, especially for use in a method of treatment of a depressive state, anxiety state, sleep disorder, vascular disorder, cerebrovascular disorder or cardiovascular disorder or for the regulation of food intake. The present invention also provides the use of a compound of formula (I), or a pharmacologically acceptable acid addition salt thereof, in the manufacture of a medicament for the treatment of a depressive state, anxiety state, sleep disorder, vascular disorder, cerebrovascular disorder or cardiovascular disorder or for the regulation of food intake. The daily dosage is generally from 1 to 1,000 mg.

The present invention finally provides a pharmaceutical composition comprising a compound of formula (I), or a pharmacologically acceptable acid addition salt thereof, and a pharmacologically acceptable excipient. The composition may be in a form suitable for oral or parenteral administration.

We claim:

1. A compound which is a pyrido[3,4-b] derivative of formula (I)

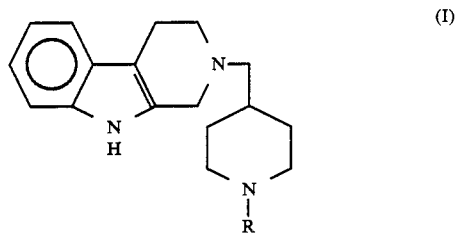

in which R is a hydrogen atom or a group of formula COR$_1$, COOR$_2$, CONHR$_3$ or SO$_2$R$_4$, wherein R$_1$ is a C$_1$-C$_6$ alkyl group, a benzyl group or a phenyl group unsubstituted or substituted with 1 to 3 substituents selected from the group consisting of halogen atoms and trifluoromethyl, C$_1$-C$_3$ alkyl and C$_1$-C$_3$ alkoxy groups, wherein R$_2$ is a C$_1$-C$_6$ alkyl group or a benzyl group, wherein R$_3$ is a C$_1$-C$_6$ alkyl group or a phenyl group, and wherein R$_4$ is a phenyl group, or a pharmacologically acceptable acid addition salt thereof.

2. A compound according to claim 1 in the form of a benzenesulphonate, hydrochloride or dichlorohydrate salt.

3. A pharmaceutical composition comprising a pharmaceutically effective amount of a compound as defined in claim 1 and a pharmaceutically acceptable excipient.

4. A method of treatment of a depressive state or anxiety state, which comprises administering to a subject suffering or liable to suffer therefrom an effective amount of a compound as defined in claim 1.

5. A method of treatment of hypertension which comprises administering to a subject suffering or liable to suffer therefrom an effective amount of a compound as defined in claim 1.

* * * * *